US008541578B2

(12) United States Patent
Guillaume et al.

(10) Patent No.: US 8,541,578 B2
(45) Date of Patent: Sep. 24, 2013

(54) PROCESS FOR THE PRODUCTION OF N-(2,6-DIMETHYL-PHENYL)-2-PIPERAZIN-1-YL-ACETAMIDE

(75) Inventors: Michel Joseph Maurice André Guillaume, Berg (BE); Jozef Ludo Jan Cuypers, Vosselaar (BE); Ivan Joseph Maria Vervest, Wuustwezel (BE); Stefan Marcel Herman Leurs, Vosselaar (BE); Dirk De Smaele, Wetteren (BE)

(73) Assignee: Janssen Pharmaceutica, N.V., Beerse (BE)

( * ) Notice: Subject to any disclaimer, the term of this patent is extended or adjusted under 35 U.S.C. 154(b) by 1775 days.

(21) Appl. No.: 10/518,887

(22) PCT Filed: Jun. 19, 2003

(86) PCT No.: PCT/EP03/50241
§ 371 (c)(1),
(2), (4) Date: Dec. 21, 2004

(87) PCT Pub. No.: WO04/000824
PCT Pub. Date: Dec. 31, 2003

(65) Prior Publication Data
US 2005/0240018 A1    Oct. 27, 2005

(30) Foreign Application Priority Data

Jun. 24, 2002    (EP) .................................. 02077749

(51) Int. Cl.
*C07D 241/00*    (2006.01)
*C07D 241/02*    (2006.01)

(52) U.S. Cl.
USPC ........................................................ 544/336

(58) Field of Classification Search
USPC ........................................................ 544/336
See application file for complete search history.

(56) References Cited

U.S. PATENT DOCUMENTS

| 3,953,448 | A |   | 4/1976  | Podesva et al. |            |
|-----------|---|---|---------|----------------|------------|
| 4,123,530 | A | * | 10/1978 | Corvi-Mora     | 514/252.12 |
| 4,558,129 | A |   | 12/1985 | Kluge et al.   |            |
| 5,382,584 | A |   | 1/1995  | Balasubramanian |           |

FOREIGN PATENT DOCUMENTS

| EP | 0126449 B1    |   | 12/1987 |
|----|---------------|---|---------|
| EP | 0582164 B1    |   | 12/1998 |
| EP | 0862566 B1    |   | 1/2000  |
| GB | 840358 A      |   | 7/1960  |
| JP | 52111583 A    |   | 9/1977  |
| WO | WO 96/40664   | * | 12/1996 |
| WO | WO 96/40664 A2 |  | 12/1996 |

OTHER PUBLICATIONS

PCT Search Report for PCT/EP03/50241 dated Nov. 20, 2003.

Hulinska et al., "Experimental Antiulcer Agents: N-Substituted 2-(4-Methyl-1-Piperazinyl) acetamides as pirenzepine models and some related compounds," Collection Czechoslovak Chem. Commun., Jan. 1988, pp. 1820-1844, vol. 53.
Moore et al., "N-Substituted derivatives of piperazine, etc. Part 1," Journal of Chemical Society, Nov. 19, 1928, pp. 39-51.
Vejdelek et al., N-(Piperazinoacyl) and N-(Piperazinoalkyl) derivatives of 4-Cyclopentylaniline and related compounds: synthesis and pharmacological screening, Collection Czechoslovak Chem. Commun., Nov. 21, 1985, pp. 1494-1502, vol. 51.
Zara-Kaczian et al. "Synthesis of 1-Aryl-1,4-Dihydro-3(2H)-ISO-Quinolinones with piperazine ring in the side chain having potential antiserotoninergic activity," Institute of Experimental Medicine, Hungarian Academy of Sciences, Mar. 1989, pp. 607-627, vol. 4.
Foye et al., "α-(N-Piperazino)dimethylacetanilides and Their Local Anesthetic Activity", Journal of Medicinal Chemistry, Jan. 1966, vol. 9, pp. 61-63.
Dritte, vollig neubearbeitete Auflage, Herausgegeben von Claudia Synowietz und Klaus Schafer, Chemiker-Kalender, Springer-Verlag, Berlin, Heidelberg, New York, Tokyo (1984), pp. 182-183, 196-197, 216-217, 282-283, 318-319, 360-361, 374-375, 528-529.
Dugos, N., AJChE 2006, vol. 6, No. 2, 98-103.
Encyclopedia of Chemical Technology, Third Edition, vol. 21, John Wiley & Sons (1983), pp. 378-387.
Handbook of Chemistry and Physics, 57th Edition, Robert C. Weast, Ph.D., 1976-1977, CRC Press, Cleveland, Ohio, C-80, C-146, C-227, C-296, C-312, C-376, C-459, C-461, C-518.
Rosano et al., JAOCS, vol. 59, No. 8 (Aug. 1982), 360-363.
http://en.wikipedia.org/wiki/Azeotrope_(data), Mar. 5, 2001.
Dritte, vollig neubearbeitete Auflage, Herausgegeben von Claudia Synowietz und Klaus Schafer, Chemiker-Kalender, Springer-Verlag, Berlin, Heidelberg, New York, Tokyo (1984), pp. 182-183, 196-197, 216-217, 282-283, 318-319, 360-361, 374-375, 528-529 [See English Translation provided: Chemist's Almanac, Third, completely revised edition, Edited by Claudia Synowietz und Klaus Schäfer, Springer-Verlag, Berlin Heidelberg New York Tokyo 1984, pp. 182-183, 196-197, 216-217, 282-283, 318-319, 360-361, 374-375, 528-529].

* cited by examiner

*Primary Examiner* — Erich A Leeser
(74) *Attorney, Agent, or Firm* — Kiera K. Mathey

(57) ABSTRACT

The present invention relates to a novel process, suitable for industrial exploitation for the production of N-(2,6-dimethyl-phenyl)-2-piperazin-1-yl-acetamide, also known as N-lidocaine, obtained from the reaction of piperazine with N-haloacetyl-2,6-xylidine. The process comprises the consecutive steps a) through f)
  a) reacting piperazine with N-haloacetyl-2,6-xylidine in a molar ratio between about 1/1 and about 6/1 in an aqueous solvent in which has been dissolved an equimolar amount of HCl;
  b) separating the solid formed in step a) from the reaction mixture;
  c) neutralizing the filtrate;
  d) extracting the filtrate with a solvent which is not or only to a small extent miscible with the aqueous solvent mentioned in step a);
  e) crystallizing the N-(2,6-dimethyl-phenyl)-2-piperazin-1-yl-acetamide from the solvent mentioned in step d) and
  f) separating the solid obtained in step e) from the solvent mentioned in step d).

6 Claims, No Drawings

PROCESS FOR THE PRODUCTION OF N-(2,6-DIMETHYL-PHENYL)-2-PIPERAZIN-1-YL-ACETAMIDE

CROSS REFERENCE TO RELATED APPLICATIONS

This application is the national stage of Application No. PCT/EP03/050241, filed Jun. 19, 2003, which application claims priority from EP 02077749.6 filed Jun. 24, 2002.

FIELD OF THE INVENTION

The present invention relates to a process for the production of N-(2,6-dimethyl-phenyl)-2-piperazin-1-yl-acetamide, a lidocaine derivative, obtained from the reaction of piperazine with N-haloacetyl-2,6-xylidine.

Such production process is known from WO 96/40664 (Dade Chemistry Systems Inc.) in which piperazine (Formula I) is reacted with N-chloroacetyl-2,6-xylidine (Formula II) to produce an oily residue that solidifies on cooling. Said process can be depicted by the reaction scheme below.

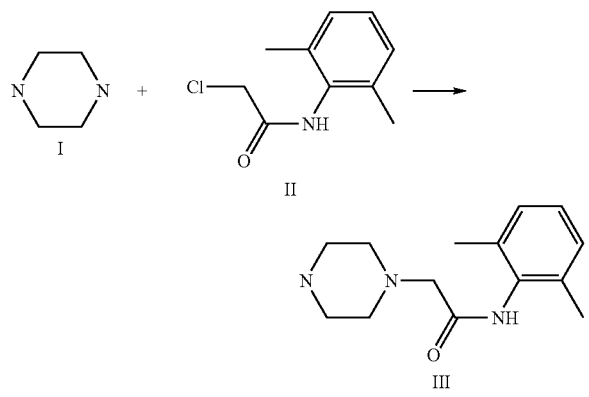

Due to the specific choice of reagents, invariably an adduct (Formula IV) is formed.

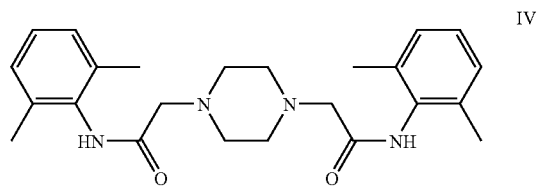 [SMILES: Cc1cccc(C)c1NC(=O)CN1CCN(CC(=O)Nc2c(C)cccc2C)CC1]

Several processes have been developed in order to reduce the amount of adduct, among which a process by which an excess of piperazine is used (WO 96/40664) and a process in which the piperazine is mono-protected (EP 126 449 B1-Syntex Inc.), EP 582 164 B1-Bristol-Myers Squibb Company).

However, all of the known methods have the disadvantage that they are not well suitable for the exploitation of the reaction on an industrial scale, in particular for a process that produces a dispersion or slurry from which the solid part can be obtained by industrial separation methods, in particular by filtration.

According to the method disclosed in WO 96/40664, the solvent in which the reaction product (Formula III) is formed needs to be removed entirely, thereby producing an oily residue, which solidifies after cooling. The entire removal of the solvent requires large amounts of energy and the formation of said solid as an oily residue is undesirable in industrial scale reactors since it is formed on the inner surfaces of the reactor, in particular on the walls and rotor blades, and therefore it is virtually impossible to remove and collect. The method disclosed in WO 96/40664 has the further disadvantage that a large excess of piperazine is used (ratio of 10/1).

Using protected piperazine is commercially undesirable because of the extra process steps needed to protect and deprotect the nitrogen.

N-(2,6-dimethyl-phenyl)-2-piperazin-1-yl-acetamide may be used as a pharmaceutical intermediate in the preparation process of 1-(1,2-disubstituted piperidinyl)-4-substituted piperazine derivatives, which are usefull as substance-P antagonists (EP 862 566 B1, Janssen Pharmaceutica NV).

The object of the present invention is to provide a process for the production of N-(2,6-dimethyl-phenyl)-2-piperazin-1-yl-acetamide obtained from the reaction of piperazine with N-haloacetyl-2,6-xylidine which is suitable for industrial scale reactors, in particular to provide a process in which the undesired adduct according to Formula (IV) or the desired end product according to Formula (III) or both are separated from the reaction mixture by filtration.

The further object of the present invention is to provide a process for the production of N-(2,6-dimethyl-phenyl)-2-piperazin-1-yl-acetamide obtained from the reaction of piperazine with N-haloacetyl-2,6-xylidine with a purity>95%.

Very surprisingly, the inventors have found that the drawbacks of the known processes can be overcome by a process which comprises the subsequent steps a) through f):

a) reacting piperazine with N-haloacetyl-2,6-xylidine in a molar ratio between about 1/1 and about 6/1 in an aqueous solvent in which has been dissolved an about equimolar amount of HCl, relative to the molar amount of piperazine;
b) separating the solid formed in step a) from the reaction mixture;
c) neutralizing the filtrate;
d) extracting the filtrate with a solvent which is not or only to a small extent miscible with the aqueous solvent mentioned in step a);
e) crystallizing the N-(2,6-dimethyl-phenyl)-2-piperazin-1-yl-acetamide from the solvent mentioned in step d) and
f) separating the solid obtained in step e) from the solvent mentioned in step d).

With the term "about" is meant a deviation of 10% or less from the given value.

Preferentially, in step a) as reagent N-chloroacetyl-2,6-xylidine is used as the latter reagent is cheap and commercially available. However, N-bromoacetyl-2,6-xylidine may also be used, as well as mixtures of them in any given ratio.

Preferentially, in step a) the molar ratio is about 3/1. Using less excess of piperazine gives a steep rise in the undesirable adduct. Using more does not essentially decrease the amount of adduct and also makes the process step a) unreasonable in terms of costs and environmental burden. With molar ratio is meant the molar amount of piperazine versus the molar amount of N-haloacetyl-2,6-xylidine Preferentially, in step a) the aqueous solvent is water, although other solvents that are totally or at least to a large extent miscible with water at the given reaction condition may also be used, such as alcohols, in particular methanol, ethanol, propanol, isopropanol, butanol and sec-butanol; THF, and acetone. Also, mixtures of different solvents may be used, for example water/alcohol, in particular water/isopropanol, in different ratios. Obviously, the solvent should be reaction-inert towards the reagents, in particular towards HCl.

Preferentially, step a) is performed by first adding an amount of HCl to a reaction mixture containing the aqueous solvent and piperazine and subsequently adding the N-haloacetyl-2,6-xylidine to the reaction mixture. The addition of HCl to the reaction mixture is an exothermic reaction. The reaction is further performed preferentially at an elevated temperature (i.e. above room temperature and below boiling temperature of the reaction mixture). Preferentially, the reaction temperature in step a) is about 60° C. to about 90° C., more preferentially about 80° C. By performing the reaction in step a) a solid is produced, which corresponds to the adduct (Formula IV). The reaction time may be chosen to be between 1-24 hours. The desirable end product according to Formula (III) is completely soluble in the reaction mixture.

In step b) the solid obtained in step a) is separated from the reaction mixture. Separation may be performed by any method known to the skilled person. Preferentially, the reaction mixture containing the solid is filtered, preferentially at an elevated temperature, more preferentially at about 60° C. By this step, the adduct is removed nearly completely while the desired end product is kept into solution.

In step c) the acidic filtrate is neutralized up to a pH>about 8. Preferentially, the acidic filtrate is neutralized to a pH equal to about 10. As neutralizing agent, any agent may be used suitable for this purpose, such as, for example a base such as sodium hydroxide, potassium hydroxide and the like.

In step d) the solvent used for the extraction is preferentially toluene. However, other solvents that are not or only to a small extent miscible with the aqueous solvent mentioned in step a) under the given reaction conditions may also be used, such as benzene, THF, methyl-t-butyl ether and methyl-ethyl ketone, as well as mixtures of them in any given ratio. Obviously, the extraction solvent should be reaction-inert. The extraction is preferably performed at elevated temperature, in particular at a temperature between room temperature and the boiling temperature of the extraction solvent used. When toluene is used, the temperature is preferentially between about 60° C. and about 80° C., more preferentially at about 70° C.

In step e) the end product is crystallized from the reaction mixture by common methods known to the skilled person. In particular, the extraction solvent may be distilled off to about ⅔ of its volume after which the temperature of the reaction mixture may be lowered, for example down to 0° C. Also, it may be appropriate to seed the reaction mixture to start the crystallization and to obtain large crystals.

Finally, in step f) the solid end product obtained in step e) can be separated from the extraction solvent by commonly known separation methods, such as filtration.

In particular, the invention relates to a process for the production of N-(2,6-dimethyl-phenyl)-2-piperazin-1-yl-acetamide obtained from the reaction of piperazine with N-chloroacetyl-2,6-xylidine, which comprises the subsequent steps a) through f):
a) reacting piperazine with N-chloroacetyl-2,6-xylidine at about 80° C. in a ratio of about 3/1 in water to which has been added 3 equivalents of HCl;
b) filtering the reaction mixture at about 60° C.;
c) neutralizing the filtrate up to a pH equal to about 10;
d) extracting the filtrate with toluene at 70° C.;
e) crystallizing the N-(2,6-dimethyl-phenyl)-2-piperazin-1-yl-acetamide from toluene and
f) filtering the solid from the filtrate.

The invention will now be illustrated by some examples and comparative experiments without being limited thereto.

Experimental

All materials were purchased from commercial suppliers and used without further purification. All reactions were conducted under an atmosphere of nitrogen. In the lab, only glass vessels are used; in the pilot plant, both steel or glass-lined vessels are used. For each reaction, a sample of the reaction mixture was collected and analysed by means of HPLC.

EXAMPLE I

Preparation of
N-(2,6-dimethyl-phenyl)-2-piperazin-1-yl-acetamide

In a 250 ml, 4-necked flask equipped with a stirrer, piperazine (12.9 g, 0.15 mol, 3 eq.) was suspended in water (15 ml, 0.1 L/mol piperazine). The mixture was stirred vigorously and $HCl_{cp}$ (12.4 ml, 0.15 mol, 3 eq.) was added cautiously (!exothermic!). The temperature rose to 45° C. and the mixture became homogeneous. After cooling to 20-25° C., N-haloacetyl-2,6-xylidine (9.9 g, 0.05 mol, 1 eq.) was added, the mixture was heated to 80° C. and stirred for 2 h. The reaction mixture was then cooled to 60° C. and filtered at that temperature over dicalite, in order to remove the precipitate of adduct. The filtrate was treated at 60° C. with NaOH 50% in water (8.5 ml, 0.16 mol, 3.2 eq., pH>10) and toluene (120 ml, 2.4 L/mol) was added. The mixture was then heated to 70° C., stirred 15 min. and the layers separated at that temperature. After discarding the water layer, about $⅔^{rd}$ of the organic phase was distilled off and the mixture slowly cooled down to 22° C. over 3 h. Seeding was performed at 60° C. The mixture was further cooled to 0-5° C. and stirred at that temperature during 1 h. The precipitate was filtered off, washed with toluene (10 ml, 0.2 L/mol) and dried during 16 h at 40° C. under vacuum. The end product was obtained as a white precipitate: m.p. 118° C.

Yield: 8.6 g (70%, 68% active yield). HPLC and base titration give satisfactory results (>97.5% purity).

$^1$H NMR ($CDCl_3$, 360 MHz) δ: 1.62 (bs, 1H, NH), 2.22 (s, 6H), 2.63 (m, 4H), 2.93 (m, 4H), 3.15 (s, 2H), 7.02-7.13 (m, 3H), 8.71 (bs, 1H, CONH)

Anal. Calcd. for $C_{14}H_{21}N_3O$: C, 67.98; H, 8.56; N, 16.99. Found: C, 68.21; H, 8.38; N, 17.22.

EXAMPLE II-XI

Effect of Different Reaction Conditions for Step a)

Step a) in the preparation according to Example I was repeated for several reaction conditions. The results are summarized in Table 1.

TABLE 1

Effect of different reaction conditions for step a).

| Example | A | B | C | D | E |
|---|---|---|---|---|---|
| II | 1/1 | 0 | $^i$PrOH (1 L/mol) | 21 h | 62% |
| III | 2/1 | 0 | $^i$PrOH (1 L/mol) | 2 h | 28% |
| IV | 3/1 | 0 | $^i$PrOH (1 L/mol) | 2 h | 28% |
| V | 2/1 | 2 | $^i$PrOH (0.66 L/mol)/$H_2O$ (0.09 L/mol) | 4 h | 17% |
| VI | 2/1 | 2.25 | $^i$PrOH (0.66 L/mol)/$H_2O$ (0.09 L/mol) | 4 h | 17% |
| VII | 2/1 | 2.5 | $^i$PrOH (0.66 L/mol)/$H_2O$ (0.09 L/mol) | 3 h | 17% |
| VIII | 3/1 | 3 | $^i$PrOH (1 L/mol)/$H_2O$ (0.135 L/mol) | 3 h | 7% |

TABLE 1-continued

Effect of different reaction conditions for step a).

| Example | A | B | C | D | E |
|---------|-----|---|----------------------------------------|------|----|
| IX | 3/1 | 3 | $^i$PrOH (1 L/mol)/H$_2$O (0.135 L/mol) | 3 h | 7% |
| X | 2/1 | 2 | H$_2$O (0.75 L/mol) | 21 h | 7% |
| I | 3/1 | 3 | H$_2$O (0.4 L/mol) | 2 h | 3% |

A: Molar ratio in step a)
B: Amount of HCl (equivalent)
C: Solvent used for the reaction in step a)
D: Reaction time (hours)
E: Amount of adduct in the reaction mixture (LC area, %)

EXAMPLE II-XI

Effect of Different Extraction and Crystallisation Media for Respectively Step d) and e)

Steps d) and e) in the preparation according to Example I were repeated for several reaction media. The results of the extractions and crystallisations (not performed consecutively) are summarized in Table 2. From this Table 2, it can be seen that although ethylacetate is suitable for extraction purposes, only toluene is suitable for extraction and crystallisation purposes, therefor obviating the need to change from extraction medium to a different crystallisation medium.

TABLE 2

Effect of different extraction and crystallisation media for respectively step d) and e).

| Solvent | Extraction | Crystallisation |
|-------------|----------------|-----------------|
| Methanol | -- | -- |
| Ethanol | -- | -- |
| Isopropanol | ○ | -- |
| N-butanol | ○ | ○ |
| sec-butanol | ○ | -- |
| Ethylacetate | ++ (at r.t.) | ○ |
| Toluene | ++ (at 70° C.) | ++ |

Qualifications:
++: very good;
+: good;
○: moderate;
--: not suitable

The invention claimed is:

1. Process for the production of N-(2,6-dimethyl-phenyl)-2-piperazin-1-yl-acetamide, obtained from the reaction of piperazine with N-haloacetyl-2,6-xylidine, characterized in that the process comprises the subsequent steps a) through f):
   a) reacting piperazine with N-haloacetyl-2,6-xylidine in a molar ratio of piperazine to N-haloacetyl 2,6-xylidine between about 1/1 and about 6/1 in an aqueous solvent in which has been dissolved in an about equimolar amount of HCl relative to the molar amount of piperazine;
   b) separating the solid formed in step a) from the reaction mixture by filtration to create a filtrate;
   c) neutralizing the filtrate;
   d) extracting the filtrate with a solvent which is not or only slightly miscible with the aqueous solvent mentioned in step a);
   e) crystallizing the N-(2,6-dimethyl-phenyl)-2-piperazin-1-yl-acetamide from the solvent mentioned in step d); and
   f) separating the solid obtained in step e) from the solvent mentioned in step d).

2. Process according to claim 1 in which N-haloacetyl-2,6-xylidine is N-chloroacetyl-2,6-xylidine.

3. Process according to claim 1, characterized in that the molar ratio in step a) is about 3/1 piperzine to N-haloacetyl-2,6-xylidine.

4. Process according to claim 1, characterized in that solvent for extraction (step d) and crystallization (step e) is toluene.

5. Process according to claim 1, characterized in that the separation method in step f) is filtration.

6. Process for the production of N-(2,6-dimethyl-phenyl)-2-piperazin-1-yl-acetamide, obtained from the reaction of piperazine with N-chloroacetyl-2,6-xylidine, characterized in that the process comprises the subsequent steps a) through f):
   a) reacting piperazine with N-chloroacetyl-2,6-xylidine at about 80° C. in water in a molar ratio of about 3/1, piperzine to N-haloacetyl-2,6-xylidine, the reaction mixture also containing an equimolar amount of HCl relative to the molar amount of piperzine;
   b) filtering the reaction mixture at about 60° C.;
   c) neutralizing the filtrate up to a pH equal to about 10;
   d) extracting the filtrate with toluene at about 70° C.;
   e) crystallizing the N-(2,6-dimethyl-phenyl)-2-piperazin-1-yl-acetamide from toluene; and
   f) filtering the solid N-(2,6-dimethyl-phenyl)-2-piperazin-1-yl-acetamide.

* * * * *

UNITED STATES PATENT AND TRADEMARK OFFICE
CERTIFICATE OF CORRECTION

PATENT NO. : 8,541,578 B2  
APPLICATION NO. : 10/518887  
DATED : September 24, 2013  
INVENTOR(S) : Guillaume et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1920 days.

Signed and Sealed this  
Third Day of March, 2015

Michelle K. Lee  
*Deputy Director of the United States Patent and Trademark Office*